US00RE37263E

(19) United States
(12) Reissued Patent
Kross et al.

(10) Patent Number: US RE37,263 E
(45) Date of Reissued Patent: Jul. 3, 2001

(54) ANTI-INFLAMMATORY FORMULATIONS FOR INFLAMMATORY DISEASES

(75) Inventors: Robert D. Kross, Bellmore, NY (US); Elliott J. Siff, Westport, CT (US)

(73) Assignee: Alcide Corporation, Redmond, WA (US)

(21) Appl. No.: 08/787,144

(22) Filed: Jan. 22, 1997

Related U.S. Patent Documents

Reissue of:
(64) Patent No.: 5,384,134
Issued: Jan. 24, 1995
Appl. No.: 08/115,461
Filed: Sep. 1, 1993

U.S. Applications:

(60) Continuation of application No. 07/930,088, filed on Aug. 14, 1992, now abandoned, which is a division of application No. 07/543,655, filed on Jun. 26, 1990, now abandoned, which is a division of application No. 07/202,758, filed on Jun. 3, 1988, now Pat. No. 4,956,184, which is a continuation-in-part of application No. 07/190,798, filed on May 6, 1988, now abandoned.

(51) Int. Cl.[7] ..... A61K 33/14; A61K 31/74
(52) U.S. Cl. ..... 424/661; 424/78.06
(58) Field of Search ..... 424/661, 78.06

(56) References Cited

U.S. PATENT DOCUMENTS

| | | | |
|---|---|---|---|
| 4,084,747 | 4/1978 | Alliger | 239/4 |
| 4,330,531 | 5/1982 | Alliger | 424/149 |
| 4,381,296 | 4/1983 | Tinnell | 424/148 |
| 4,540,567 | 9/1985 | Oneto et al. | 424/45 |
| 4,690,772 | 9/1987 | Tell et al. | 252/106 |
| 5,185,161 | 2/1993 | Davidson | 424/665 |

FOREIGN PATENT DOCUMENTS

WO 88/01507 3/1988 (WO) .

OTHER PUBLICATIONS

M.S. Abdel Rahman et al., "Toxicity of alcide," *J. Appl. Toxicol.* 2(3): 160–164, 1982 (Dialog abstract).

Scatina et al., "Pharmacodynamics of Alcide, a New Antimicrobial Compound, in Rat and Rabbit," *Fundamental and Applied Toxicology* 4:479–484, 1984

*Primary Examiner*—Theodore J. Criares
(74) *Attorney, Agent, or Firm*—Seed and Berry LLP

(57) ABSTRACT

There is disclosed a method for treating dermatologic diseases caused by microbial overgrowth or inflammation, such as psoriasis, fungal infections, eczema, dandruff, acne, genital herpes lesions, and leg ulcers. There is further disclosed an antiviral lubricating composition that is effective in preventing the transmission of the HIV virus and other sexually transmitted diseases. There is also disclosed systemic and anti-inflammatory compositions and formulations and a method for reducing tissue inflammation in tissues such as the bowel, muscle, bone, tendon and joints (e.g., arthritis).

10 Claims, 4 Drawing Sheets

ANTI-INFLAMMATORY FORMULATIONS FOR INFLAMMATORY DISEASES

Matter enclosed in heavy brackets [ ] appears in the original patent but forms no part of this reissue specification; matter printed in italics indicates the additions made by reissue.

CROSS-REFERENCE TO RELATED APPLICATION

This application is a continuation of U.S. Ser. No. 07/930,088, filed Aug. 14, 1992, now abandoned; which is a divisional of U.S. Ser. No. 07/543,655, filed Jun. 26, 1990, abandoned; which is a divisional of U.S. Ser. No. 07/202,758, filed Jun. 3, 1988; which issued as U.S. Pat. No. 4,956,184; which is a continuation-in-part of U.S. Ser. No. 07/190,798, filed May 6, 1988, abandoned.

TECHNICAL FIELD

This invention relates generally to topical formulations that are useful for treating various dermatologic disorders, including genital herpes lesions, facial and body acne, topical fungal infections, psoriasis, eczema, dandruff, skin ulcers (e.g., decabutus), and other dermatologic diseases associated with microbial proliferation. This invention also relates to the anti-inflammatory properties and uses of pharmaceutical compositions.

BACKGROUND OF THE INVENTION

There are a Large number of dermatological diseases that are thought to be caused by microbial overgrowth somehow result in a dermatologic infection and/or inflammatory reaction. These diseases include acne vulgaris and other pilosebaceous inflammatory disorders, which are thought to be caused in part by an overgrowth of the anaerobic bacterium Propionibacterium acnes (P. acnes), which is normally present in the sebaceous follicles but proliferates in large numbers during acute acne. P. acnes generates a lipase, a protease, and other potentially damaging substances. Follicular contents are known to be chemo-attractive for leukocytes, and complement activation is probably also important in the inflammatory process. Although the precise mechanisms are not entirely clear, inflammation and edema in the follicular wall result in follicular rupture, leaking follicular contents into the surrounding dermis and creating further inflammation. The visible consequence of this series of dermal events is a deep inflammatory nodule, called a "cyst." An accumulation of neutrophils in the mouth of a follicle produces a pustule. Deep inflammatory or cystic lesions may arise from preexisting closed comedones in an area of normal-appearing skin.

Genital herpes is also called "Herpes Progenitalis" and is caused by the herpes simplex virus, usually type 2. Primary genital herpes follows an incubation period of 3 to 7 days. The disease can be found by localized burning or paresthesia and followed by eruption of grouped vesicles, often at multiple sites on the genitalia. The lesions generally heal in 2 to 4 weeks, but the virus remains in the nerve heads and can remain dormant or trigger secondary lesions by migrating down the nerve fiber to the nerve ending to reproduce into more lesions. Recurrent genital herpes is common after the primary infection. Secondary lesions heal within two weeks, and secondary attacks become less frequent with time. Treatments include drying agents to symptomatically lessen the discomfort of the lesion. Acyclovir, applied topically, tends to decrease pain of the primary lesions, but it has not proven very effective for decreasing vital shedding or lesion duration. Topical acyclovir has not been shown to be particularly effective for reducing or treating recurrent disease.

Acyclovir is a purine nucleoside analog that is selectively cidal to the herpes simplex virus because only the thymidine kinase enzyme of herpes simplex virus can convert acyclovir to its monophosphate form while host cell thymidine kinase cannot. The monophosphate form is converted to an acyclovir triphosphate, which can interfere with vital DNA replication. Topical acyclovir is applied as a 5% ointment every three hours, or up to eight times daily, for at least seven days. The up to eight-times-a-day dosing is a difficult procedure for patients and creates patient compliance problems for dosing in the genital areas throughout the day and throughout the night. A further problem of acyclovir has been the development resistant strains of herpes simplex, caused by a mutation of the thymidine kinase gene. Accordingly, no backup treatments are available for acyclovir-resistant herpes simplex infections. This problem exists with most antibiotic microbial treatments, but is generally not a problem non-antibiotic treatments.

Topical fungal or yeast diseases represent a large class of diseases. These can include tinea versi color, which is a superficial fungal infection caused by the lipophilic yeast Pityrosporum orbiculare. The infected areas do not pigment normally and produce a whitish, spotted appearance in dark-skinned or tanned persons. Treatments include the use of dandruff shampoos on the affected areas and typical antifungal agents, including the imidazole derivatives miconazole and clotrimazole. Fungal lesions on the skin surface are named "tinea" and the Latin name of the particular type of location. For example, "tinea capitis" is for scalp lesions, while "tinea cruris" is for groin lesions. Tinea cruris is often manifest as symmetrical scaly patches on the inner surfaces of the thighs. The infection spreads with a central clearing area and a sharply demarcated border. Itching is common and severe. The major causitive organisms are T. rubrum, T. mentagrophytes, and Epidermophyton floccsum.

Tinea pedis is commonly called "athlete's foot." It is often caused by Trichophyton rubrum or Trichophyton mentagrophytes. It often begins as a scaly lesion between the toes and spreads to produce an acute inflammatory vesicular disease, accompanied by itching, burning and pain. Tineas corpotis is also called "ringworm" and is a dermatophyte infection involving nonspecific areas of skin. The infection is an erythematous, scaly patch on the skin with sharp, acute borders and central clearing. Current treatments for topical fungal diseases include the imidazole derivatives, miconazole and clotrimazole. Griseofulvin is a systemic agent, and ketoconazole is also used systemically but is expensive and is associated with severe side effects. Side effects of griseofulvin include headaches and abdominal discomfort.

Eczema is a superficial inflammation of the skin characterized by an initial erythematous, papulovesicular process often accompanied by oozing and crusting and followed by a chronic phase of scaling, thickening and post-inflammatory pigment changes. Causes of eczema are largely uncertain but can include fungal infection. Treatments are largely symptomatic and can include topical corticosteroids for the inflammatory reaction.

Psoriasis is a papulosquamous disease characterized by chronic periodic remissions and exacerbations. Lesions usually consist of erythematous plaques with silvery scale, and possibly a pustular form. The causes of psoriasis include several theories. One theory advances that psoriasis is an inflammatory overreaction to a yeast infection, such as that caused by P. ovale. The disease is characterized histologically by accelerated cellular turnover. Psoriasis is a chronic condition and an affected individual can develop lesions at any time. Treatments vary, depending on what one believes is the cause of the disease. However, no single treatment has yet proven to be successful for a wide variety of cases.

Dandruff is a scaling condition of the scalp. It is thought to be caused by an overgrowth of P. ovale, a yeast. Treatment is usually an antimicrobial agent such a pyrithione zinc, a keratolytic agent such as salicylic acid, or by a cytostatic agent such as a coal tar.

Statis dermatitis is a leg ulcer and is a form of eczema and often the result of venous insufficiency. It often develops in a patch just distal to where a vein was removed for a bypass procedure. Treatment is usually with a topical steroid or with an antibacterial and keratolytic agent, such as 20% benzoyl peroxide.

Acquired Immune Deficiency Syndrome (AIDS) is believed to be spread by sexual contact, and more specifically, through transmission of the HIV virus. The current preventive means for transmission by sexual contact with an individual suspected of harboring the HIV virus is a barrier, such as a condom. At present, there are no known virucidal chemical barrier preparations available that can be used alone or with a condom for prevention of the spread of HIV during sexual contact.

Anti-inflammatory agents are usually classified as steroid or non-steroidal agents. The non-steroidal anti-inflammatory agents most often function by inhibition of prostaglandin or leukotriene biosynthetic pathways. For example, non-steroidal anti-inflammatory drugs such as aspirin (acetylsalicylic acid), indomethacin, and ibuprofen are known to inhibit the fatty acid cyclooxygenase enzyme in the prostaglandin pathway from arachidonic acid. Steroid drugs have anti-inflammatory activity but also have numerous side effects, including sodium retention, hepatic deposition of glycogen, and dramatic redistribution of body fat. The steroid anti-inflammatory properties are mediated by inhibiting edema, fibrin deposition, capillary dilation, migration of leukocytes, and deposition of collagen. Steroid anti-inflammatory agents have immunosuppressant side effects.

While it is difficult to give an adequate description of the inflammatory phenomenon in terms of the underlying cellular events in the injured tissue, there are certain features of the process that are generally agreed to be characteristic. These include fenestration of the microvasculature, leakage of the elements of blood into the interstitial spaces, and migration of leukocytes into the inflamed tissue. On a macroscopic level, this is usually accompanied by the clinical signs erythema, edema, tenderness (hyperalgesia), and pain. During this complex response, chemical mediators such as histamine, 5-hydroxytryptamine (5-HT), slow-reacting substance of anaphylaxis (SRS-A), various chemotactic factors, bradykinin, and prostaglandins are liberated locally. Phagocytic cells migrate into the area and cellular lysosomal membranes may be ruptured, releasing lytic enzymes. All these events may contribute to the inflammatory response. However, aspirin-like drugs have little or no effect upon the release or activity of histamine, 5-HT, SRS-A, or lysosomal enzymes; and similarly, potent antagonists of 5-HT of histamine have little or no therapeutic effect on inflammation.

The inhibitors of prostaglandin biosynthesis by aspirin and other non-steroidal anti-inflammatory agents, such as ibuprofen, has been demonstrated in three different systems, cell-free homogenates of guinea pig lung, per fused dog spleen, and human platelets. There are now numerous systems in vitro and in vivo in which inhibition of prostaglandin biosynthesis by aspirin, ibuprofen, or similar compounds has been demonstrated, and it is evident that this effect is not restricted to any one species or tissue. The effect is dependent only on the drug reaching the enzyme, cyclooxygenase (prostaglandin synthetase); the distribution and pharmokinetics of each agent thus have an important bearing on the drug's activity.

The migration of leukocytes into inflamed areas is an important component of inflammation. Although the classical aspirin-like drugs (salicylates, pyrazolone derivatives, ibuprofen, indomethacin, etc.) block prostaglandin biosysthesis, they do not inhibit the formation of the major chemotactic metabolite of arachidonic acid, HETE, and may even increase concentrations of this compound in tissue.

Hypoxia and ischemia are inevitable fates of any kind of tissue injury. Oxygen tension in tissue wounds, when measured by implanted polarographic oxygen electrode, was found to be only 5 to 15 mm Hg, as compared to control tissue values of 40 to 50 mm Hg. (Sheffield, "Tissue Oxygen Measurements with Respect to Soft Tissue Wound Healing with Normobaric and Hyperbaric Oxygen," Hyperbaric Oxygen Rev. 6:18–46, 1985.) Tissue ischemia is associated with an inflammatory response mediated by stimulated Hagemann factor arid complement cascades. (Weiss et al., "Phagocyte-Generated Oxygen Metabolites and Cellular Injury", Lab Invest. 47:5–18, 1982.) These factors activate polymorphonuclear leukocytes (PMNs) and result in a massive influx of phagocytic leukocytes into the wound. Paradoxically, the antimicromial properties of PMNs are greatly impaired in the ischemic wound region in vivo because of the lack of molecular oxygen. (Mandell, "Bactericidal Activity of Aerobic and Anaerobic Polymorphonuclear Neutrophils," Infect. Immunol. 9:337–41, 1974.) Oxygen therapy, including hyperbaric oxygen treatment, has been suggested to facilitate wound healing and is often used as adjunctive therapy in problem wounds and wound infections. However, the optimal times and mode of oxygen therapy still remain clouded. Oxygen radicals are involved in the phagocytic actions of PMNs, which, upon activation, generate superoxide and hydroxyl radicals as well as hydrogen peroxide and hypochlorous acids at the site phagocytosis.

Any wounding, whether surgical or traumatic causes disruption of blood vessels, tissue hemorrhage, activation of Hageman factor, and stimulation of complement pathways. These morphologic and biochemical events result in the massive influx of PMNs into the wound site and the production of superoxide radicals by PMNs as part of the phagocytic response [Reaction (i)]. The generated superoxide radicals undergo the Haber-Weiss reaction [Reaction (ii)] or iron-catalyzed Fenton type reactions [Reaction (iii)], producing cytotoxic OH radicals and $H_2O_2$, which ultimately form hypohalite radicals via the myeloperoxidase, system [Reaction (iv)].

i.

$$NADPH + 2O_2 \xrightarrow[\text{oxidase}]{NADPH} NADP^+ + 2O_2^- + H^+$$

ii.

$$H_2O_2 + O_2^- \longrightarrow OH^- + OH'' + O_2$$

-continued iii.

$$Fe^{2+} + H_2O_2 \longrightarrow Fe^{3+} + OH'' + OH^-$$

iv.

$$H_2O_2 + Cl^- + H^+ \xrightarrow[\text{peroxidase}]{\text{mvelo}} H_2O + HOCl$$

Although the presence of these oxygen-free radicals is necessary for the oxidative killing of microorganisms, excessive generation of these cytotoxic radicals may be extremely harmful to native tissues. Tissues are generally equipped with adequate antioxidative defense systems, consisting of such enzymes as superoxide dismutase, catalase, and glutathione peroxidase. However, these antioxidative enzymes are known to be reduced during ischemia and hypoxia.

Accordingly, there is a need in the pharmaceutical art for a therapeutic agent that has both strong and broad spectrum antimicrobial properties for a wide variety of bacterial, fungal, vital, and yeast infections, as well as anti-inflammatory activity, yet not be an antibiotic with the risk of developing resistant microbial strains. It is further desirable to develop a chemical agent that can be used as an antimicrobial sexual barrier and lubricating gel that has strong antiviral properties to kill active HIV virus and thereby help prevent the spread of AIDS. There is also a need in the pharmaceutical art for an anti-inflammatory therapeutic agent that does not possess the side effect problems of the aspirin-like non-steroidal anti-inflammatory agents or the immunosuppressant properties of the corticosteroids.

SUMMARY OF THE INVENTION

The aforementioned therapeutic problems are treated by a strongly antimicrobial and anti-inflammatory formulation wherein the active antimicrobial and/or anti-inflammatory effects are provided by a composition which comprises a chlorine dioxide liberating compound and a protic acid. Preferably, the chlorine dioxide liberating compound is an alkaline metal chlorite. Most preferably, the chlorine dioxide generating compound is sodium chlorite or potassium chlorite. Topical formulations are useful for the topical treatment of dermatologic disorders thought to be caused by overgrowth of pathogenic microorganisms that possibly result in an inflammatory response, or for inflammatory conditions. These dermatologic disorders include topical fungal diseases, vital lesions such as from genital herpes, and inflammatory/bacterial disorders such as acne. Additionally, the formulations containing the active agents of the present invention are useful for the treatment of decubitus ulcers, psoriasis, eczema and as an antimicrobial sexual lubricant to prevent the transmission of sexually transmitted diseases, such as HIV (AIDS), chlamydia, genital herpes, warts, gonorrhea, and syphilis. Systemic formulations that are administered orally, or by injection into muscles, joint capsules, peritoneum, intralymphatically or directly into inflamed tissue. The inventive formulations have an added benefit of broad spectrum antimicrobial activity.

All of the formulations involve infusion, tissue, dermatologic or topical uses of a formulation containing chlorous acid in metastable balance, which provides chlorine dioxide as the active antimicrobial and anti-inflammatory agent. The formulations involve two solutions, gels, or creams adapted to be mixed and either infused or injected into the site of activity, taken orally, or topically applied so as to adhere to the epithelial surface and penetrates into the dermis. The first solution, gel, or cream contains an amount of metal chlorite, such that, when combined in equal parts with the first gel, the chlorite ion concentration in the form chlorous acid is no more than about 15% by weight of the total amount of chlorite ion concentration. The second solution, gel, or cream contains an aqueous solution containing suitable amounts of a protic acid. Preferably, the first gel contains a polysulfonic acid wherein the anion of the salt has the formula:

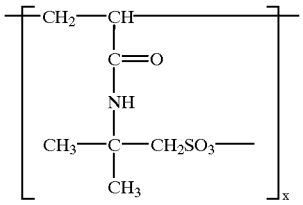

wherein X has a value such that the molecular weight of the anionic portion of the polymer is from about 1,000,000 to about 5,000,000 daltons.

DETAILED DESCRIPTION OF THE INVENTION

Figure 1:
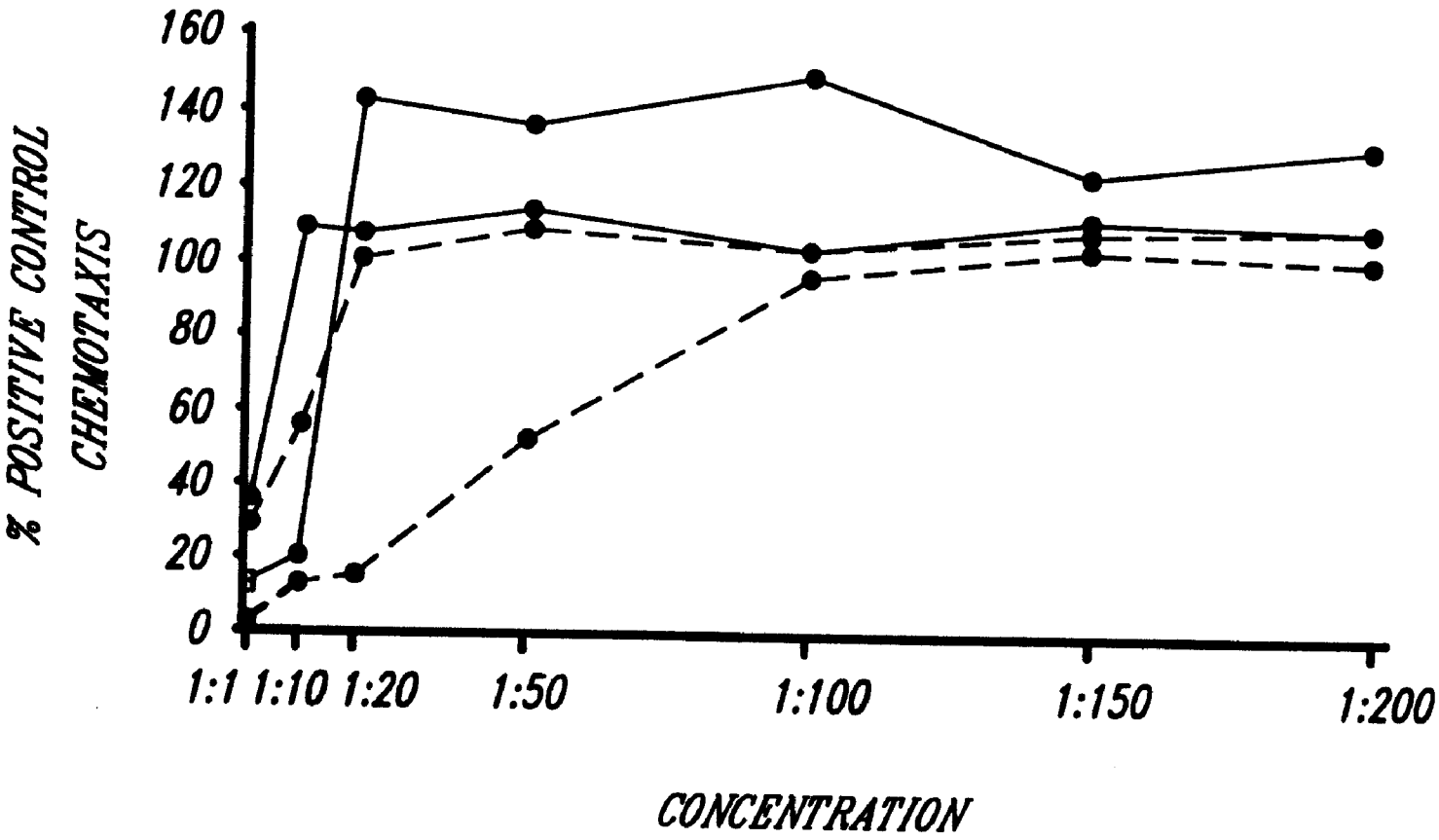
FIG. 1 shows the in vitro chemotaxis of the inventive composition at the active concentration of Example 1 and the non-steroidal anti-inflammatory agent ibuprofen (0.5 mg/ml). The inventive composition is shown by ●—● and ibuprofen by ■—■. When there is a dotted Line, the inventive composition and ibuprofen were reacted with BSA (bovine serum albumin).

The compositions described herein are useful as topical formulations to treat human skin disorders caused by microbial overgrowth or by inflammation. The skin disorders include facial or body acne, topical fungal infections, genital herpes, psoriasis, leg and decubitus ulcers, eczema, and dandruff. The composition can function as a lubricating barrier gel for the prevention of transmission of sexually transmitted diseases. Dandruff, psoriasis, and eczema are hyperproliferative or inflammatory disorders that are believed to be initiated by, or associated with fungal or yeast microbial overgrowth. Accordingly, the skin disorders are often caused by microorganisms, including bacterial, viral, yeast and fungal sources. The compositions or formulations are also useful as anti-inflammatories.

The therapeutic compositions are useful for the treatment of skin diseases that involve an inflammatory and/or a microbial proliferation component or both components.

Thus, the topical application of the inventive compositions containing a chlorine dioxide liberating compound in one solution, cream, or gel and a protic acid in the other solution, cream, or gel, when mixed, yield chlorine dioxide that is the active antimicrobial or anti-inflammatory agent. A gel composition should have superior skin-adherence properties.

Topical application of the therapeutic compositions described herein relates to application to the surface of the skin and to certain body cavities such as the mouth, vagina, colon, bladder, nose, and ear.

Systemic application can be localized directly by injection into inflamed tissue, such as the joint for arthritis or encapsulated in an enteric-coated capsule that can release its contents in the intestine after passing through the stomach.

The therapeutic compositions and formulations described herein are useful for the treatment of inflammatory disorders. For example, inflammatory disorders caused by influx of PMNs into a wound site can be inhibited by the inventive compositions and formulations. Similarly, ibuprofen, a nonsteroidal anti-inflammatory agent also has been found to inhibit PMN influx into inflammatory tissues. The inhibition of PMN influx into a wound site can simultaneously reduce the formation of malondialdehyde and conjugated dienes, suggesting that most of the free radicals generated during the early stage of wound healing are mediated by PMNs. The majority of PMNs have been found to reach the site of inflammation at the early stage of tissue injury. The compositions and formulations of the present invention comprising a chlorine dioxide liberating compound in a protic acid inhibited the rate of PMN influx into the wound site during the healing process. The decrease in PMN influx was accompanied by the reduced formation of malondialdehyde and conjugated dienes, implying a simultaneous reduction in free radical formation. Accordingly, the ability of the inventive compositions and formulations to inhibit PMN influx into a wound site is evidence of anti-inflammatory activity.

One aspect of the inventive process is for the treatment of skin disorders caused by microbial overgrowth or inflammation, such as acne, psoriasis, eczema, genital herpes simplex lesions, topical fungal infections, decubitus and leg ulcers and dandruff, with a formulation comprising two solutions, creams, or gels. The first solution, cream, or gel contains a pharmaceutically effective amount of a chlorine dioxide generating compound. The second solution, cream, or gel contains an effective amount of a protic acid to maximally and controllably release chlorine dioxide from the chlorine dioxide generating compound, chlorous acid, formed when the two solutions, creams, or gels are mixed. Preferably, the first and second solutions are aqueous solutions.

The inventive process applies a composition formed by the combination of the first gel, cream, or solution and the second gel, cream, or solution. Preferably, the dermatologic composition is formed by the combining of the first and second gels. More preferably, the first gel, containing the chlorine dioxide releasing compound, has a metal chlorite and a polysulfonic acid salt. The final concentrations of chlorite and acid are relatively low. The final concentration range of chlorite concentration from about 100 ppm to about 5000 ppm. Preferably, the final range of chlorite concentration is from about 800 ppm to about 1600 ppm. The final concentration range of acid is from about 0.1% w/w to about 5% w/w. Preferably, the final concentration range of acid is from about 0.5% w/w to about 1.3% w/w.

A second aspect of the inventive process is for the treatment of inflammatory disorders such as arthritis, interstitial cystitis, and inflamed bowel by specifically localizing the inventive composition to the inflamed tissue. This can be accomplished, for example, by injecting the mixed solution directly into the joint capsule or by simultaneously injecting both the first and second solutions with a double syringe and needle of the type disclosed in U.S. Pat. No. 4,330,531. Thus the first and second solutions will mix at the site of injection and locally form chlorous acid for modulated release of chlorine dioxide. Alternatively, the solutions can be mixed prior to administration and delivered by G-I tube infusion (orally or rectally) to the inflammed section of the G-I tract. A further delivery mode is by encapsulation in a specially coated pharmaceutical matrix that is designed to release its contents in the small intestine upon oral administration.

The composition provides a metastable chlorous acid composition formed from small amounts of chlorite, preferably from a metal chlorite, and acid, preferably an organic acid with a pK from about 2.8 to about 4.2. The composition is capable of generating chlorine dioxide over an extended time up to about 24 hours, at continuing levels of effectiveness. As chlorine dioxide forms, more of the chloride converts to chlorous acid by interacting with hydrogen ions further generated by ionization of the organic acid.

Weak organic acids which may be used in the second solution or gel to form the composition of the inventive process include citric, malic, tartaric, glycolic, mandelic and other structurally similar acids as described in Formula I hereinbelow:

FORMULA I

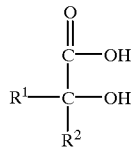

$R^1$ and $R^2$ may be the same or different and may be selected from the group consisting of hydrogen, methyl, $—CH_2COOH$, $—CH_2OH$, $—CHOHCOOH$, and $—CH_2C_6H_5$. Compositions of a metal chlorite and the weak organic acids of Formula I are disclosed in copending U.S. patent application Ser. No. 850,009, filed on Apr. 10, 1986. The entire disclosure of that application is hereby incorporated by reference.

The second gel, containing the protic acid, also contains a gelling agent or thickener which is well known to those skilled in the art. Any gelling agent or thickener which is nontoxic and nonreactive with the other ingredients of the composition may be used, such as cellulose gels, typically methyl cellulose, or preferably, hydroxy ethyl cellulose. Furthermore, that gel may also contain a preservative, such as benzyl alcohol or sodium benzoate. Other additives, such as buffers to adjust the pH of the composition to become more compatible with the skin, may be used.

The amount of thickener in the second, protic acid-containing gel may be generally from about 0.5% to about 5%, typically from about 0.8% to about 4%, and preferably from about 1% to about 3% of the gel, by weight, of the total composition. The amount of preservative in the gel may be generally from about 0.1% to about 0.05%, typically from about 0.01% to about 0.04%, and preferably from about 0.02% to about 0.03% by weight of the total composition. The chlorine dioxide liberating compound or metal chlorite and the protic acid are present in separate gels, and the amount of the preservative is present in only that gel containing the protic acid.

The first gel, containing a metal chlorite, is preferably thickened with a polysulfonic acid salt. The amount of polysulfonic acid salt added will depend on the desired use of the resulting composition. The amount of polysulfonic acid salt is generally from about 5% to about 15%, typically from about 5% to about 10%, and preferably from about 6% to about 8% by weight of the total composition. The polysulfonic acid is prepared from:

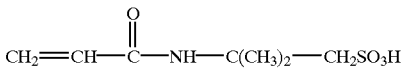

or a salt thereof. The polymerization reaction may be accomplished by a solution, emulsion, or suspension polymerization process. The medium for the polymerization is water, an alcohol, or a mixture thereof. The polymerization reaction is described in copending U.S. patent application Ser. No. 038,016, filed Apr. 14, 1987 and incorporated by reference herein.

The treatment of certain skin diseases or certain body cavity and joint inflammatory conditions can be additionally accomplished by the synergistic combination of the chlorous acid/chlorine dioxide formed upon admixture of the two gels, creams or solutions and from the protic acid itself. For example, the composition for acne contains salicylic acid as the protic acid in the second gel. It is known that salicylic acid is a keratolytic agent useful for its desquamatory properties in the treatment of acne. Further, another protic acid useful for topical treatments is lactic acid, which also functions to form chlorous acid from the metal chlorite, from which chlorine dioxide is formed.

The gel, cream, or solution containing the protic acid (second gel, cream, or solution) and the gel, cream, or solution containing the metal chlorite (first gel, cream, or solution) are mixed either before application to the affected skin area or in situ. After the gels, creams, or solutions are mixed, the pH of the final mixture composition is generally less than about 7, typically from about 2 to about 5, and preferably from about 2.5 to about 4. In the treatment process, the mixture composition is ordinarily applied to the affected skin area at a level of about 0.00.1 gram to about 0.1 gram per square centimeter of the affected substrate.

The present invention also encompasses a method of treatment of certain skin diseases, wherein the mixture composition of two creams, solutions or gels is applied topically to affected skin at least once daily. Preferably, the mixture composition is applied topically to affected skin twice daily (e.g., b.i.d.). The mixture composition should not be applied to affected skin more than eight times a day.

The present invention is illustrated by the following examples. Unless otherwise noted, all parts and percentages in the examples as well as the specification and claims are by weight.

EXAMPLE 1

This example illustrates a formulation useful for the topical treatment of genital herpes according to the methods of the present invention. This formulation also can be used for hemorrhoids and has anti-inflammatory activity, as shown in Examples 7–9. There is prepared a two-part topical composition according to the invention, having a first gel with sodium chlorite as the chlorine dioxide liberating agent and a second gel with lactic acid as the activator protic acid. The formulations on a percent weight basis are as follows:

| | % |
|---|---|
| First Gel | |
| Poly (sulfonic acid) (16% solution ± 1%) | 45.0 |
| Sodium hydroxide 1 N | 45.0 |
| Sodium chlorite (80% ± 5%) | 0.32 |
| Tetrasodium EDTA | 0.19 |
| Water | q.s. |
| Second Gel | |
| Lactic Acid (38% ± 5%) | 2.64 |
| Natrosol 150 MR | 1.75 |
| Isopropyl alcohol U.S.P. | 5.0 |
| Poloxamer 188 | 0.4 |
| Sodium Benroate | 0.04 |
| Water | q.s. |

EXAMPLE 2

The composition of Example 1 was prepared for a clinical trial in a pair of unit dose sachets. A 2-gram quantity of gel containing 0.16% of active chlorite was prepared by mixing the contents of both sachets immediately prior to application. Thirty-five patients (30 males and 5 females) were enrolled. Thirty-four were diagnosed as having active genital herpes. Thirty-one patients complied with the treatment of twice daily dosing for seven days. Three patients received the compositions of Example 1 t.d.s., and one patient defaulted. Patients were examined daily until the lesions were healed (defined as re-epithelialization of the original lesions). The results of the study were compared to a similar study conducted with topical acyclovir and placebo (Fiddian et al, J. Antimicrob. Chem. 12:Suppl. B:67–77, 1983) and are presented together in Table 1 below:

| | Median Duration of Symptoms (d) | Median Viral Shedding Time (d) | Median Healing Time (d) | Recurrence Rate % |
|---|---|---|---|---|
| Example 1 (32) | 3* | 1** | 8 (1–17) | 19.4 |
| Acyclovir | 5 | 3 | 7–8 | 35 |
| Placebo | 8 | 6–9 | 10–13 | 55 |

*Twenty-one of twenty-four patients had a duration of symptoms of 5 or less days.
**Sixteen of twenty-two patients had viral shedding time of 1 day or less.

Clinically, 34/35 patients were suffering from first episode (primary) herpes. One patient had a typical lesion (ulcer) which was infected with Haemophyllis ducryiae which crusted over and failed to respond to treatment with the composition of Example 1. The treatment was virologically effective and patient compliance was good. Positive factors mentioned by the patients influencing compliance were:

twice daily dosing (compared with 5 times daily with some treatments such as Acyclovir)

the formation of a dry protective film over the lesions; reduction of odor; and sanitizing effect.

EXAMPLE 3

The following formulation can be used as a dermatologic gel for psoriasis treatment:

| | % |
|---|---|
| Base | |
| Sodium chlorite (80% ± 5%) | 0.32 |
| Tetrasodium EDTA | 0.19 |
| Poly (sulfonic acid) (16% solution ± 1%) | 45.0 |
| Sodium hydroxide 1 N | 40.0 |
| Nacconol 90F | 1.8 |
| Water | q.s. |
| Activator | |
| Propylene glycol U.S.P. | 40.0 |
| Salicylic acid U.S.P. | 2.0 |
| Poloxamer 188 | 0.4 |
| Sodium Benzoate | 0.04 |
| Natrosol 250 MR | 2.1 |
| Isopropyl alcohol U.S.P. | 5.0 |
| Water | q.s. |

EXAMPLE 4

The following formulation can be use as an acne treatment gel:

| | % |
|---|---|
| Base | |
| Sodium chlorite (80% ± 5%) | 0.32 |
| Tetrasodium EDTA | 0.19 |
| Poly (sulfonic acid) (16% solution ± 1%) | 45.0 |
| Sodium hydroxide 1 N | 40.0 |
| Nacconol 90F | 1.8 |
| Water | q.s. |
| Activator | |
| Salicyclic acid U.S.P. | 2.0 |
| Isopropyl alcohol U.S.P. | 30.0 |
| Natrosol 250 MR | 2.1 |
| Poloxamer 188 | 0.4 |
| Sodium benozate | 0.04 |
| Water | q.s. |

EXAMPLE 5

The following gel can be used for topical fungal infections, including tinea cruris:

| | % |
|---|---|
| Base | |
| Sodium chlorite (80% ± 5%) | 0.32 |
| Tetrasodium EDTA | 0.19 |
| Nacconol 90F | 1.8 |
| Poly (sulfonic acid) (16% solution ± 1%) | 45.0 |
| Sodium hydroxide 1 N | 45.0 |
| Water | q.s. |

-continued

| | % |
|---|---|
| Acitvator | |
| Maadeiic acid | 2.0 |
| Poloxamer 188 | 0.4 |
| Sodium benzoate | 0.04 |
| Natrosol 250MR | 1.75 |
| Water | q.s. |

EXAMPLE 6

The following cream cam be used for the topical treatment of leg or decubitus ulcers, topical fungal infections, vaginitis, psoriasis and eczema:

| | % |
|---|---|
| Base | |
| Sodium chlorite (80% ± 5%) | 0.32 |
| Tetrasodium EDTA | 0.19 |
| Glycerol monostearate | 4.0 |
| Gincam E-20 disearate | 3.0 |
| Poly (sulfonic) acid (16% solution ± 1%) | 15.0 |
| Sodium hydroxide 1 N | 15.0 |
| Water | q.s. |
| Activator | |
| Lactic acid (80% ± 5%) | 2.64 |
| Natrosol 250 MR | 1.25 |
| Isopropyl alcohol U.S.P. | 5.0 |
| Giueam E20 disearate | 3.0 |
| Glycerol monostearate | 4.0 |
| Cetyl alcohol | 8.0 |
| Stearyl alcohol | 2.0 |
| Sodium benzoate | 0.04 |
| Water | q.s. |

EXAMPLE 7

This example illustrates that a composition with the active ingredient concentration of Example 1, at concentrations greater than 1:10 dilution with water, inhibits 90% of PMN chemotaxis as shown in FIG. 1. The chemotaxis inhibiting activity decreases with increasing dilution. At the 1:20 dilution with water, a composition with the active ingredient concentration of Example 1 inhibits 60% PMN chemotaxis, whereas after a 1:50 dilution, very little anti-inflammatory activity is noted. Similarly, the known anti-inflammatory agent, ibuprofen, inhibits 50% PMN chemotaxis at a 0.12 mM concentration. When diluted to 0.048 mM or further, ibuprofen shows very little anti-inflammatory activity.

PMNs were obtained from rabbit blood and purified as described in Bandyopadhyay et al., "$^{111}$Indium-Tropolone Labeled Human PMNs: A Rapid Method of Preparation and Evaluation of Labeling Parameters," Inflammation 11:13–22, 1987). Rabbit blood was drawn from the ear vein of four donar rabbits (50 ml each), mixed with acid citrate dextrose (ACD) anticoagulant and 10 ml of Hespan (6% HETASTARCH), and stood at room temperature for 45 minutes to allow spontaneous settling of the Fed blood cells. As rabbit blood appears to be homologous, blood was pooled for purposes of obtaining PMN cells for labelling. The upper layer was collected and centrifuged at 150 g for 8–10 minutes. The upper plasma layer was saved in a different tube and centrifuged at 450 g for 10 minutes to obtain platelet-poor plasma (PPP) and in the labeling of PMNs with $^{111}$Inoxine. The pellet was resuspended in 0.9% saline, and residual red blood cells were lysed by lowering the tonicity with three volumes ice water for 30 seconds. Tonicity was restored by adding one volume Hank's Balanced Salt Solution (HBSS) containing 10 mM buffer, pH 7. The PMNs were then isolated by a single-step density gradient centrifugation method, using Ficoll-Hypaque mixture of density 1.114.

Sixty to eighty microcuries of Indium-$^{111}$-oxime (specific activity greater than 10 mCi/ug) (Mediphysics, Inc., Emeryville, Calif.) were incubated with PMNs ($3\times10^6$) in PPP at 37° C. for 20 minutes. Labeled cells were centrifuged and washed to remove unbound $^{111}$Inoxine prior to injecting the PMNs into the ear veins of the rabbits studied. The viability of the PMSs prior to and following $^{111}$In-labeling was checked in vitro by the conventional trypan blue dye exclusion method in vitro leukocyte chemo taxis was accessed using the modified Boyden Chamber Assay. (Zigmund et al, "Leukocyte Locomotion and Chemotaxis," J. Exp. Med. 137:387–410, 1983.)

EXAMPLE 8

Figure 2:
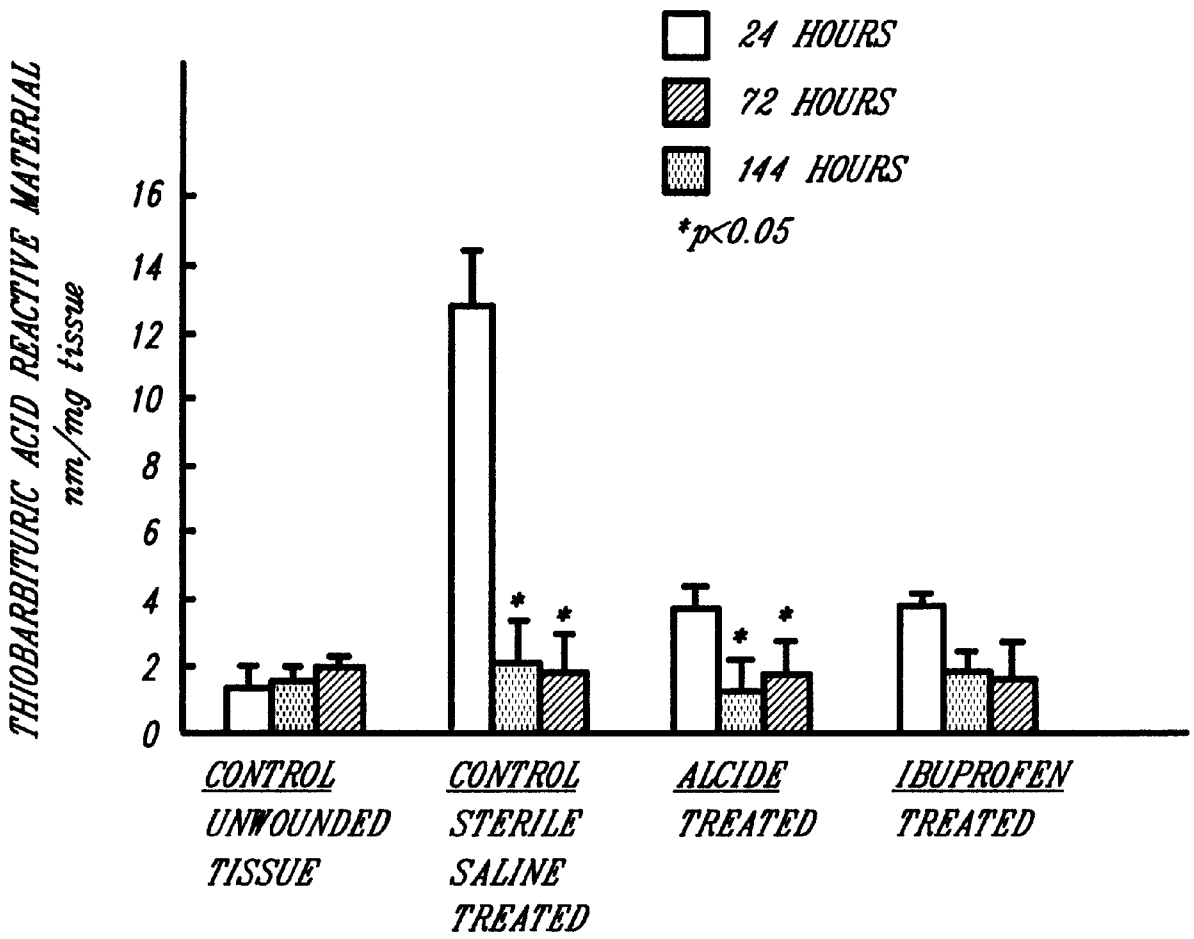
FIG. 2 shows the effect of the inventive composition (called "Alcide") and ibuprofen on the thiobarbituric acid-reactive material production at the wound site during the healing process.
Figure 3:
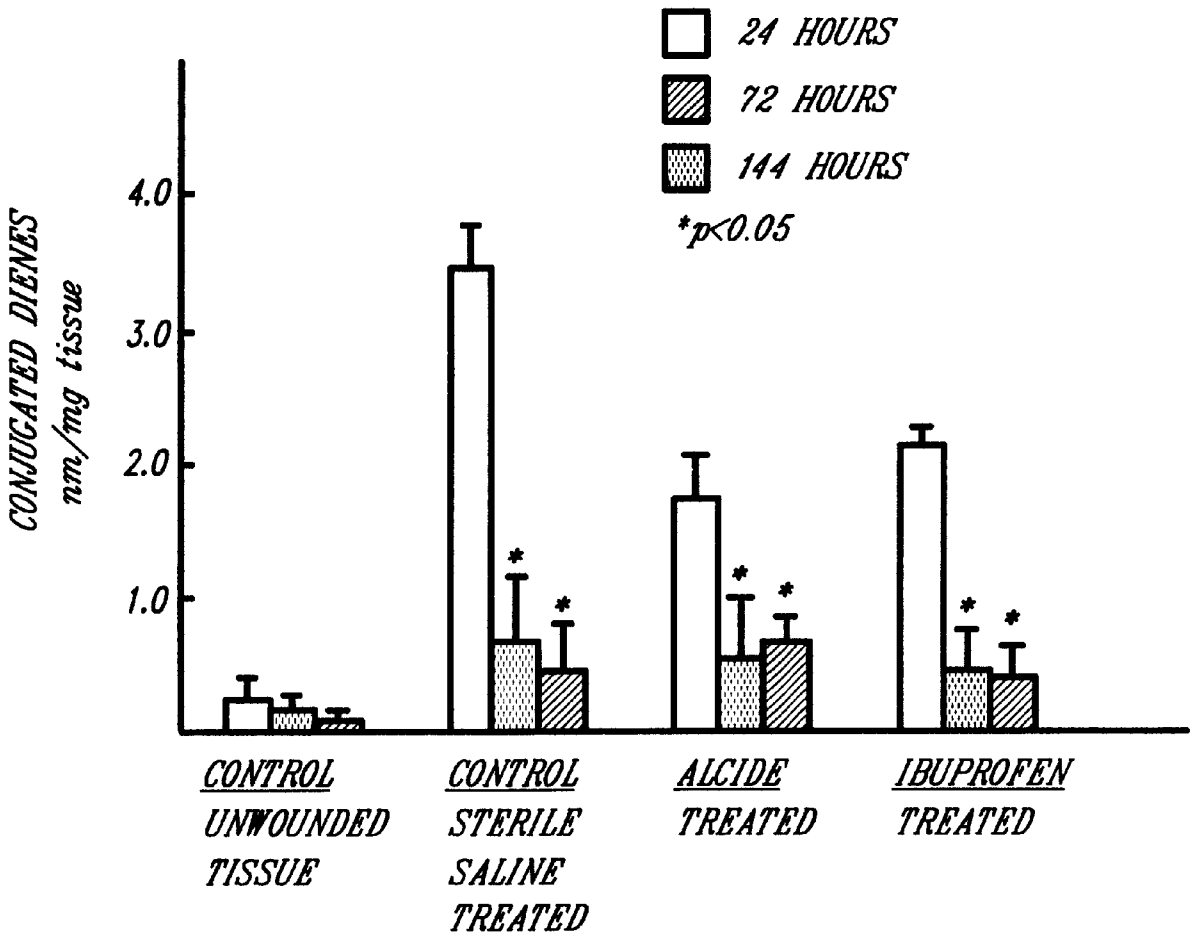
FIG. 3 shows the effect of the inventive composition (called "Alcide") and ibuprofen on the conjugated dienes formation at the wound site during the healing process.

Both ibuprofen and the composition of Example 1 were able to reduce the formation of oxygen-free radicals in vivo as indicated by the concentrations of malondialdehyde and conjugated dienes in tissue biopsies from wound regions and from nonwound areas. Very little malondialdehyde and conjugated dienes were noticed in the biopsies from nonwound regions, while appreciable amounts of these two compounds were found in the wound biopsy regions. See FIGS. 2 and 3. FIGS. 2 and 3 indicate the formation of free radicals in the wound area decreases with the duration of the healing process. Maximum concentrations of malondialdehyde in conjugated dienes were noticed in 24-hour wound biopsies, with a progressive decline in later biopsies (days 3 and 6). The activities decreased with time, suggesting the presence of decreased free radicals with the duration of healing time.

In this example malondialdehyde was assayed as described in Das et al., "Affects of Superoxide Anions on The (Na+K)ATPase System in Rat Lung," Clin. Physiol. Biochem. 2:32–38, 1984. Each tissue sample was weighed and added to 15% trichloroacetic acid (TCA) (30 mg/ml). Tissue was homogenized using a Polytron homogenizer at 0°–5° C. in an ice bath. The contents were transferred to screw cap test tubes. One ml of 0.75% thiobarbituric acid solution in 0.5% sodium acetate was then added to each tube. The tubes were boiled in a water bath for 20 minutes. The samples were centrifuged. Absorbance of supernatants was read at 535 nm. The molar extinction coefficient at 535 nm equaled 156 $mM^{-1}cm^{-1}$. The results are expressed as nmoles of thiobarbituric acid reactive material formed per gram of tissue.

The assay for superoxide generation was done according to the modified method of McCord et al, "The Reduction of Cytochrome C by Milk Xanthine Oxidase," J. Biol. Chem. 243:5733–60, 1968. Aliquots of cell suspension containing $5\times10^6$ cells/ml (PMNs) were introduced into 12×75 nm polypropylene test tubes. These cells were activated in the presence of $1.0^{-7}$M FMLP(formyl-methionyl-leucyl-phenylalanine, chemotactic factor). The cells plus the activator were incubated for 20 minutes in the presence of 75 uM horse heart ferricytochrome C (Type III, Sigma). Incubation was terminated by placing the tubes on ice, following which they were centrifuged at 800 g for 10 minutes at 4° C. To determine cytochrome C reduced by the presence of superoxide anion during the incubation, 0.2 ml of cell free of supernatant was mixed with 2.2 ml of buffer (pH 7.9), and the absorbance measured at 550 nm in a Beckman recording spectrophotometer. The amount of cyctochrome C in the reaction mixture was calcuated using an absorbance coefficient of 21.1 $mM^{-1}cm^{-1}$ at 550 nm and expressed as nmole of cytochrome C reduced per $10^6$ cells. The reagent blank contained the same mixture without the cells, and the absorbance of the nonreduced cytochrome C was subtracted from the total reaction mixture.

The assay for conjugated diene is described by Recknagel et al, "Lipoperoxidation As a Vector in Carbon Tetrachloride Hepatotoxicity," Lab. Invest. 15:132–46, 1966.

EXAMPLE 9

Figure 4:
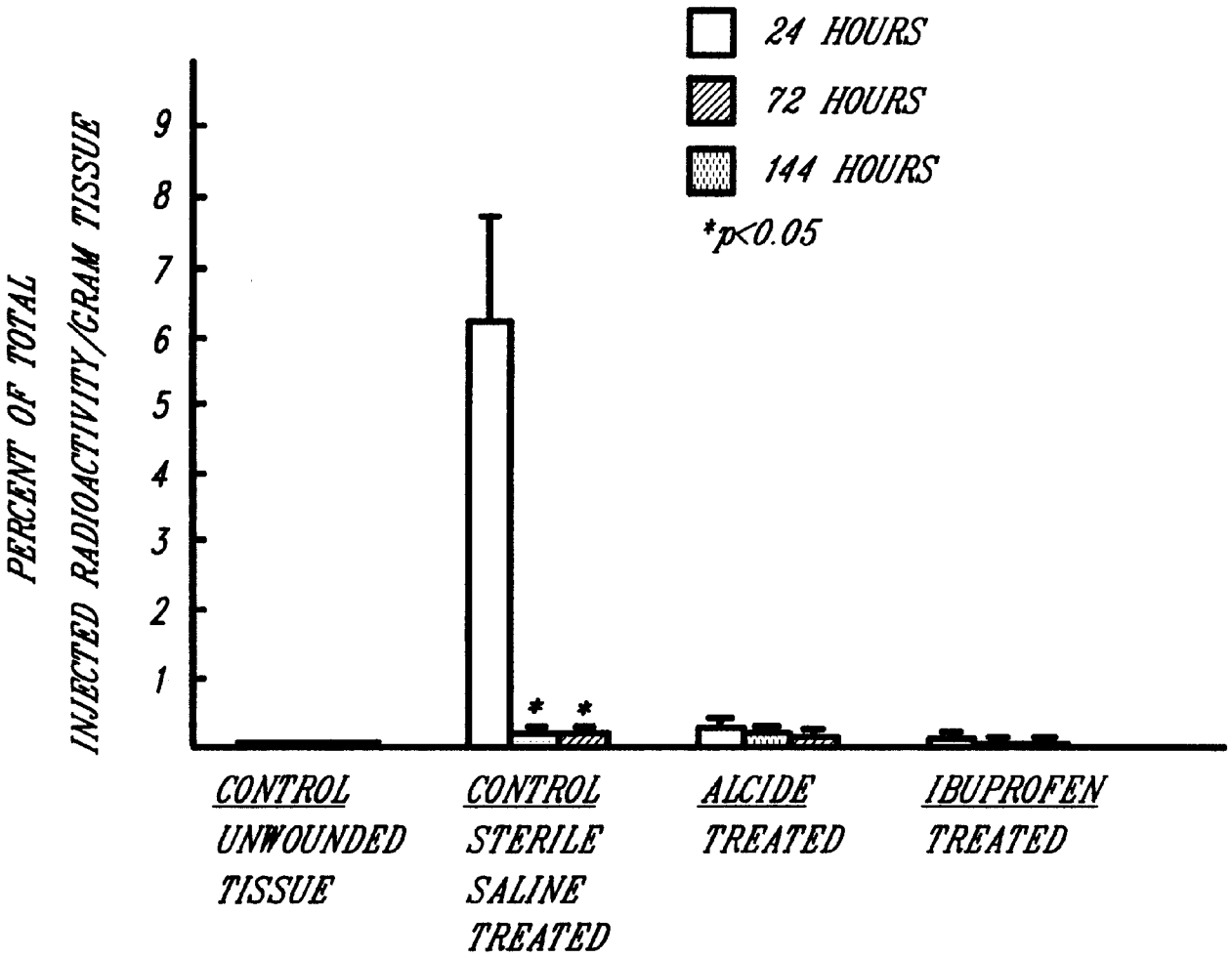
FIG. 4 is a scintigraphic comparison of Indium-111-radioactivity accumulation at the wound site during the healing process. The inventive composition is termed "Alcide." Gamma-scintigraphy was performed 4 hours following the Indium-111-labeled PMN injection. Images were digitized in a 128×128 matrix, and regions of interest in wound and nonwound areas were studied.

This example illustrates that significant influx of radiolabeled PMNs into the wound region occurred within hours of surgical incision. See FIG. 4. The influx of PMNs decreased with the duration of the healing process, and very little PMN occurred after three days of wound healing. The results by noninvasive, whole-body gamma-scintigraphy was confirmed by counting the radioactivity incorporated in wound and nonwound regions of tissue biopsies. See Table 2 below:

TABLE 2

Effects of the Composition of Example 1 and Ibuprofen on the In Vivo PMN Influx in the Wound Biopsies Evaluated by Organ Counting

| | Day 1 | Day 3 | Day 6 |
|---|---|---|---|
| | (% of injected dose/gram tissue wt) | | |
| Control | 7.165 ± 1.121 | 0.906 ± 1.003 | 0.007 ± 0.007 |
| Example 1 | 0.011 ± 0.005 | 0.034 ± 0.022 | 0.006 ± 0.002 |
| Ibuprofen | 0.020 ± 0.010 | 0.007 ± 0.002 | 0.008 ± 0.009 |

A significantly higher amount of radioactivity was found in the wound biopsies compared to nonwound biopies. A reduced amount of radioactivity was found in the ibuprofen and Example 1 composition treated wounds. The amount of $^{111}$Indium-radioactivity was maximum in the 24-hour wounds, confirming the results of whole-body gamma-scintigraphy.

The principles, preferred embodiments, and modes of operation of the invention have been described in the foregoing specification. However, the invention herein which is intended to be protected is not to be construed as limited to the particular forms disclosed, since these are to be regarded as illustrative rather than restrictive. Variations and changes may be made by those skilled in the art without departing from the spirit and scope of the invention.

What is claimed is:

1. A method for reducing tissue inflammation comprising topically applying a pharmaceutically effective amount of an anti-inflammatory composition comprising a mixture of a first solution, cream, or gel consisting essentially of a chlorine dioxide liberating compound and a second solution, cream, or gel consisting essentially of a protic acid, wherein the chlorine dioxide liberating compound comprises a metal chlorite, and wherein the chlorite ion concentration in the form of chlorous acid is no more than about 15% by weight of the total amount of chlorite ion concentration in the composition and wherein the gel or cream optionally contains a thickener.

2. The method of claim 1 wherein the pK of the protic acid is from about 2.8 to about 4.2.

3. The method of claim 1 wherein the first solution, cream, or gel is a gel and contains a polysulfonic acid salt as a thickener.

4. A method for treating inflammatory disorders comprising locally administering a pharmaceutically effective amount of a composition comprising a first solution or gel consisting essentially of a chlorine dioxide liberating compound, and a second solution or gel consisting essentially of a protic acid, wherein the chlorine dioxide liberating compound comprises a metal chlorite, and wherein the chlorite ion concentration in the form of chlorous acid is no more than about 15% by weight of the total amount of chlorite ion concentration in the composition and wherein the gel or cream optionally contains a thickener.

5. The method of claim 4 wherein the pK of the protic acid is from about 2.8 to about 4.2.

6. The method of claim 5 wherein the chlorine dioxide liberating compound is sodium chlorite.

7. The method of claim 4 wherein the inflammatory disorder is selected from the group consisting of arthritis, lupus, bowel inflammation, tendon inflammation and muscle inflammation.

*8. The method of claim 1 wherein the tissue inflammation is a viral lesion.*

*9. The method of claim 8 wherein the viral lesion is a herpes lesion.*

*10. The method of claim 1 wherein the tissue inflammation is a wound site.*

* * * * *